United States Patent
Kikuchi et al.

(10) Patent No.: US 7,432,110 B2
(45) Date of Patent: Oct. 7, 2008

(54) MICROCHANNEL ARRAY

(75) Inventors: Yuji Kikuchi, 8-1-1-1902, Minamisenju, Arakawa-ku, Tokyo (JP) 116-0003; Mitsutoshi Nakajima, Ibaraki (JP); Taiji Nishi, Tokyo (JP); Motohiro Fukuda, Ibaraki (JP)

(73) Assignees: National Agriculture and Food Research Organization, Tsukuba-shi (JP); Kuraray Co., Ltd., Kurashiki-shi (JP); Yuji Kikuchi, Tokyo (JP)

( * ) Notice: Subject to any disclaimer, the term of this patent is extended or adjusted under 35 U.S.C. 154(b) by 0 days.

(21) Appl. No.: 11/659,952

(22) PCT Filed: Aug. 4, 2005

(86) PCT No.: PCT/JP2005/014304

§ 371 (c)(1),
(2), (4) Date: Feb. 12, 2007

(87) PCT Pub. No.: WO2006/016519

PCT Pub. Date: Feb. 16, 2006

(65) Prior Publication Data

US 2007/0276972 A1    Nov. 29, 2007

(30) Foreign Application Priority Data

Aug. 12, 2004    (JP) ............................ 2004-235134

(51) Int. Cl.
*G01N 1/18*    (2006.01)

(52) U.S. Cl. ................ 436/177; 422/100; 422/102
(58) Field of Classification Search ............... 436/177
See application file for complete search history.

(56) References Cited

U.S. PATENT DOCUMENTS

| 5,730,187 | A  * | 3/1998 | Howitz et al. ............... 137/803 |
| 6,258,858 | B1 * | 7/2001 | Nakajima et al. ............. 516/73 |
| 2005/0167370 | A1 | 8/2005 | Nakajima et al. |

FOREIGN PATENT DOCUMENTS

| JP | 2000-023657 | 1/2000 |
| JP | 2002-027969 | 1/2002 |
| JP | 2005-080607 | 3/2005 |
| WO | WO2004/037399 A2 * | 5/2004 |

* cited by examiner

*Primary Examiner*—Walter D. Griffin
*Assistant Examiner*—Bobby Ramdhanie
(74) *Attorney, Agent, or Firm*—Oblon, Spivak, McClelland, Maier & Neustadt, P.C.

(57) ABSTRACT

A microchannel array according to the present invention includes a first substrate 1, and a second substrate 11 bonded to the first substrate 1. Two sets, that is, a set of a first through-hole 9, a first recess 7, and a first groove 8 and a set of a second through-hole 4, a second recess 2, and a second groove 3 are formed on the first substrate 1. The different sets are separated by a partition 5. A cell differentation/proliferation speed after micro-injection can be increased by using such microchannel array.

11 Claims, 7 Drawing Sheets

MICROCHANNEL ARRAY

TECHNICAL FIELD

The present invention relates to a microchannel array, and more particularly to a microchannel array used for a suction trap of cells or other such particles.

BACKGROUND ART

A technique of transferring genes to a cell as typified by micro-injection is the key to improving bleeding efficiency of animal and plant species and microbial species having useful characteristics. Thus, various transferring methods have been developed hitherto from the viewpoints of reliability and efficiency.

For example, the inventors of the present invention developed such technique that a microcapillary array where a number of injection probes are regularly arrayed, and a microchamber array having chambers corresponding to the probes are used to collectively inject DNAs to all cells held in the micro chamber array for the purpose of enhancing operation (see Patent Document 1). However, according to this method, it is difficult to sufficiently cover variations in shape, size, and elasticity between cells. In some cases, the injection probe cannot be inserted to a cell, or if inserted, the insertion depth is too small or large, with the result that DNAs cannot be collectively injected. Further, a probe insertion direction and a direction in which an observer observes a target portion with a microscope are substantially the same. This makes it difficult to insert a probe while observing a target portion with a microscope in practice. Even if the target portion can be observed with a microscope, a probe moves in a focal depth direction of the microscope, leading to a problem that an image is blurred due to the movement and its positional control is difficult.

To that end, the inventors of the present invention have made extensive studies in view of operational reliability and developed a microchannel array capable of suction trap of cells or other such particles at an opening edge of a substrate end surface (see Patent Document 2). If the microchannel array is used, during micro-injection, the probe movement direction and the observation direction of the microscope are substantially orthogonal to each other, so the injection can be carried out while observing with the microscope. Thus, DNA or other such substances can be more reliably and readily injected.

However, the above microchannel array has a possibility that cells are damaged upon suction trap of the cells. Further, although the microchannel array is suitable for micro-injection, the array is inappropriate for incubation of cells prior to the injection or differentiation/proliferation of cells after the injection. Thus, it is necessary to culture cells in another place prior to the injection, and to carry out differentiation/proliferation of cells in another place after the injection, resulting in a problem that the total efficiency of the operation is low. Another serious problem is that a cell differentiation/proliferation speed cannot be increased.

[Patent Document 1] Japanese Unexamined Patent Application Publication No. 2000-23657

[Patent Document 2] Japanese Unexamined Patent Application Publication No. 2002-27969

DISCLOSURE OF THE INVENTION

Problems to be Solved by the Invention

As described above, the conventional microchannel array has a problem that a cell differentiation/proliferation speed cannot be increased. The present invention has been accomplished in view of the above problems, and an object of the invention is to provide a microchannel array capable of increasing a cell differentiation/proliferation speed.

Means for Solving the Problems

The above object is attained by a microchannel array containing a first substrate, and a second substrate bonded to the first substrate with a particle trap opening edge being formed in an end surface of the first substrate by a groove formed in a bond surface of the first substrate, including: (a) a first through-hole passed through the first substrate, a first recess including the first through-hole, and a plurality of first grooves communicating with the first recess and the end surface of the first substrate; (b) a second through-hole passed through the first substrate, a second recess having the second through-hole, and a second groove communicating with the second recess and the end surface of the first substrate; and (c) a partition separating the first recess from the second recess, at the bond surface of the first substrate, the second groove being formed between the plurality of adjacent first grooves with the partition between the second groove and the first grooves.

Advantages of the Invention

According to the present invention, it is possible to provide a microchannel array capable of increasing a cell differentiation/proliferation speed.

DESCRIPTION OF REFERENCE NUMERALS

1 FIRST SUBSTRATE
2 SECOND RECESS
3 SECOND GROOVE
4 SECOND THROUGH-HOLE
5 PARTITION
6 BOUNDARY BLOCK
7 FIRST RECESS

8 FIRST GROOVE
9 FIRST THROUGH-HOLE
10 END SURFACE
11 SECOND SUBSTRATE
15 THIRD GROOVE
20 CELL

BEST MODES FOR CARRYING OUT THE
INVENTION

Hereinafter, embodiments of the present invention will be described with reference to the accompanying drawings. The following description aims at illustrating preferred embodiments of the present invention and is not construed as limiting the scope of the present invention to the embodiments. In the following description, substantially the same components are denoted by like reference numerals.

In a microchannel array according to the present invention, cells or other such particles are suction-trapped at an edge of a particle trap opening formed in a first substrate end surface. As a result, upon micro-injection, a micropipette movement direction (substantially horizontal direction) and an observation direction of a microscope (vertical direction) are substantially orthogonal to each other to thereby enable observation with high magnification and control of a leading edge of the micropipette within a focal depth. Both of transmitted illumination and reflected epi-illumination can be used for the observation with a microscope. The cell or other such particles can be observed with transmitted illumination and in addition, a microchannel side where recesses or grooves are formed can be observed with the reflected epi-illumination. Therefore, DNA or other such substances can be more reliably and readily injected.

Further, first grooves are formed on both sides of a second groove for trapping cells or other such particles with a partition therebetween. For example, a fresh culture solution can be continuously supplied to cells or other such particles trapped to the second groove through a first through-hole and a first recess from the first groove. Hence, after the cells or other such particles are suction-trapped in the culture solution, and micro-injection is carried out, the cells or other such particles can be cultured as they are in the culture solution, so a series of operations can be executed with much higher efficiency.

Figure 1:
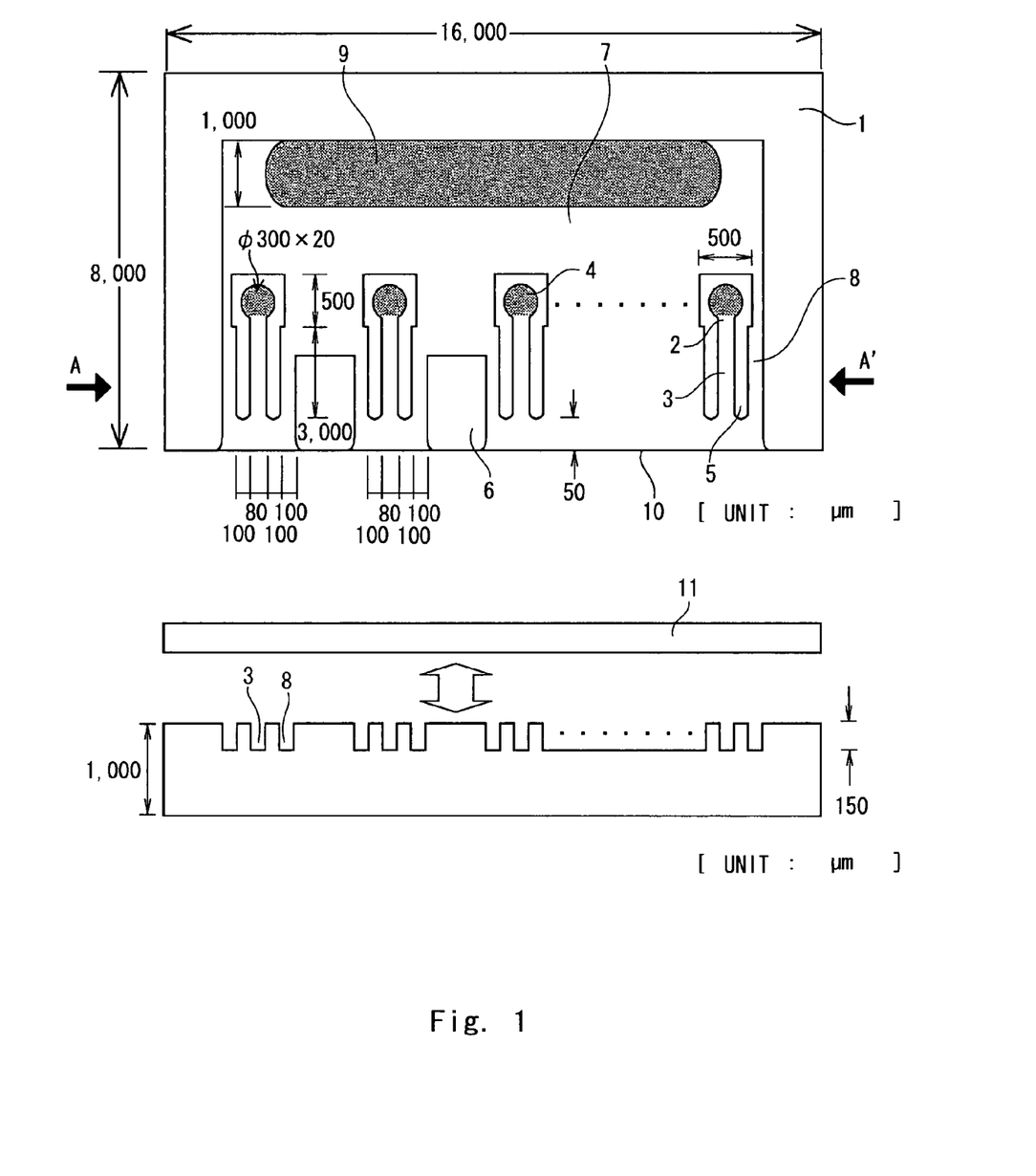
FIG. 1 shows the structure of a microchannel array A according to the present invention.

Referring to FIG. 1, the structure of the first substrate is described next. FIG. 1 shows the structure of a microchannel array of the present invention. An upper portion of FIG. 1 is a top view of the first substrate 1 used in the microchannel array of the present invention. A lower portion of FIG. 1 is a side sectional view of how the first substrate 1 and a second substrate 11 are bonded into a microchannel array. FIG. 1 shows all dimensions in μm. A first through-hole 9 for supplying a cell culture solution is formed at the center of the first substrate 1. The first through-hole 9 is formed in a first recess 7. Then, a first groove 8 extends from the first recess 7 to an end surface 10 of the first substrate 1. Thus, the first through-hole 9, the first recess 7, and the first groove 8 communicate with one another. A culture solution is supplied from the rear side of the first through-hole 9 to thereby flow into the first groove 8 through the first recess 7. The first groove 8 extends up to the end surface 10 of the first substrate 1, so the culture solution flows out from the end surface 10. That is, the first groove 8 functions as a microchannel for supplying a culture solution. As for the first groove 8, two grooves are paired, and plural first grooves are formed. The first grooves 8 are arranged at regular intervals, and an interval between adjacent groove pairs is also constant.

A substantially U-shaped partition 5 is formed in an area surrounded by the two first grooves 8 and the first recess 7. A second groove 3 for sucking cells is provided between the two first grooves 8 with the partition 5 therebetween. The second groove 3 functions as a microchannel for sucking cells or other such particles. On the other hand, a second through-hole 4 used for suction is formed in the partition 5. The second through-hole 4 is formed in the second recess 2. That is, the second through-hole 4, the second recess 2, and the second groove 3 communicate with one another. Cells or other such particles are sucked from the rear side of the second through-hole 4 and thereby sucked to the edge of the second groove 3. A boundary block 6 regulating the width of the first groove 8 is provided between the first grooves 8 of the adjacent pairs. That is, the first groove 8 width corresponds to a distance between the partition 5 and the boundary block 6.

The pair of first grooves 8, the second groove 3 formed between the pair of first grooves 8 and the second recess 2 corresponding to the second groove 3 form one microchannel group, and plural microchannel groups are arranged along the end surface 10 of the first substrate 1. That is, in one microchannel group, three grooves constituting the microchannel are formed. Then, the second groove 3 is formed between the pair of first grooves 8. Accordingly, one microchannel group realizes one coaxial microchannel structure. That is, the first grooves 8 are formed on both sides of the second groove 3 to attain the coaxial structure. The structure is repeatedly formed on the bond surface of the first substrate 1, and thus a coaxial microchannel array having a plurality of pairs of two microchannels is obtained. The pair of first grooves 8 may be arranged asymmetrically to the second groove 3 of the microchannel array, or the number of grooves on one side may be larger than that on the other side.

Here, the edge of the partition 5 is within the end surface 10. Thus, the first groove 8 and the second groove 3 communicate with each other around the end surface 10. The edge of the boundary block 6 reaches the end surface 10 and partitions the adjacent pair of first grooves 8.

The first substrate 1 and the second substrate 11 are bonded with their bond surfaces opposite to each other. In general, the substrates are closely bonded such that the end surface of the second substrate 11 is substantially aligned with the end surface 10 of the first substrate. The second substrate 11 is, for example, a transparent glass substrate or acrylic resin substrate. This facilitates observation with a microscope. In such state that the first substrate 1 and the second substrate 11 come into close contact, there is an opening between the adjacent boundary blocks 6. Then, cells or other such particles are trapped by being sucked from the second through-hole 4. That is, a particle trap opening edge is positioned at the second groove 3. The edge of the partition 5 is within the end surface 10, so a space for cell differentiation/proliferation is defined around the end surface 10. The space is a recess formed in the end surface 10 of the first substrate 1, and its width is defined by an interval between adjacent boundary blocks 6. Further, the space depth is determined based on a distance from the partition 5 to the end surface 10, and its height is determined based on a depth of an area where the first groove 8 and the second groove 3 communicate with each other.

The height of the space may be equal to or a little smaller or larger than a size of a cell or other such particles as a suction-trap target. The cell is trapped to a narrow space to thereby grow a cell within a short culture period.

Figure 2:
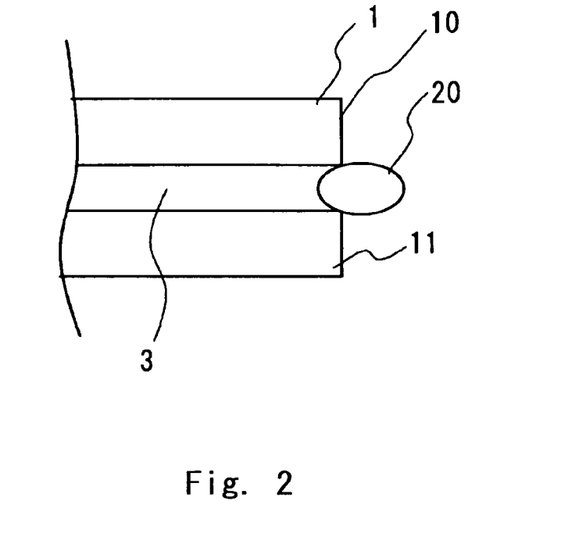
FIG. 2 is a side sectional view showing how the microchannel array A of the present invention sucks a cell.

FIG. 2 shows how a cell 20 is trapped to the end surface 10. In such state that the first substrate 1 and the second substrate 11 come into close contact, an opening is formed in the end surface 10 in an area corresponding to the second groove 3. Here, if sucked from the rear side of the second through-hole 4, the cell 20 is trapped to the opening edge and held. That is, the cell 20 is partially caught into the space for cell differentation/proliferation. However, the width of the second groove 3 is somewhat smaller than that of the cell 20, so the cell 20 is trapped at the edge of the partition 5 as the edge of the second groove 3. Further, the cell 20 partially extends from the end surface 10 of the first substrate 1. Thus, the cell can be easily observed with a microscope, and in addition, genes or other such substances can be correctly injected through micro-injection. At this time, the cell 20 partially occupies an area surrounded by the partitions 5 on both sides thereof, the first substrate 1, and the second substrate 11, so a culture solution from the first groove 8 does not flow into the second groove 3 and not weaken an effect of sucking the cell from the second through-hole 4.

In general, it is known that a cell differentation/proliferation speed varies depending on a size of the space for differentation/proliferation in a cell incubation/organization test. Therefore, it is preferred that the space for trapping the cell have substantially the same size as that of a suction-trap-target cell. Hence, the cell differentation/proliferation speed can be increased.

Preferably, the edge of the partition 5 is within the end surface 10 of the first substrate. On the other hand, it is preferred that the edge of the boundary block 6 be positioned closer to the end surface 10 side than the edge of the partition 5. For example, in the structure of FIG. 1, the width between the partitions 5 is 80 μm. Thus, a cell having a size of, for example, about 100 μm is caught in the partitions 5 on both sides thereof and suction-trapped to the second groove 3. After that, if the cell is stabilized and its size exceeds that of the second groove 3, the cell is sandwiched between the first substrate 1 and the second substrate 11. If the cell becomes larger, the boundary block 6 serves as a guide to immobilize the cells. In this state, even if the suction force of the suction trap is reduced, the cell position is not changed, and a cell coat or the like can be prevented from being damaged due to the suction trap. Moreover, a cell differentiation/proliferation speed can increase.

The height of the space for cell stabilization/differentiation/proliferation is determined based on the depth of the first groove 8 and the second groove 3, the width of the space is determined based on an interval between adjacent boundary blocks 6, and the depth of the space is determined based on a distance from the end surface 10 to the edge of the partition 5. In general, the height, width, and depth of the space are preferably within a range of 0.1 to 300 μm, more preferably 1 to 200 μm.

The width and depth of the first groove 8 and the second groove 3 of the microchannel are preferably within a range of 0.1 to 300 μm, more preferably 1 to 200 μm. Further, a ratio between the width and depth of the groove is preferably selected within a range of 1:10 to 10:1 as appropriate based on a shape or deformability of a target cell or other such particles.

If the first substrate 1 and the second substrate 11 are brought into close contact when in use, impurities such as a cell fragment coexist with a cell sample. Thus, there is a fear that the impurities are sucked to clog a suction port. To prevent this clogging, both substrates may be laminated and brought into close contact instead of completely bonding these substrates through the application of ultrasonic wave, laser, or heat. If so, the substrates can be separated and washed after used, clogged impurities can be readily removed, and the substrates can be reused.

The microchannel array of the present invention is structured such that grooves of the bond surface of the first substrate are arranged in parallel along the end surface 10. Owing to such structure, micro-injection efficiency can be more enhanced. That is, even when some suction ports are clogged with impurities such as a cell fragment, if cells or other such particles are suction-trapped to other ports, the micro-injection can be continued.

In the microchannel array of the present invention, as in the structure of FIG. 1, first recesses 7 are formed and connected to the plural first grooves 8 arranged in parallel, with the result that the first grooves 8 communicate with each other. The first recess 7 has a first through-hole 9. It is possible to form plural first through-holes 9, but the number of first through-holes 9 is preferably small from the viewpoint of manufacturing costs of a microchannel array. Further, in the case of supplying a culture solution or the like from the first through-hole 9, it is necessary to execute positional alignment between a culture solution supply port and the first through-hole 9. Thus, it is preferred that the number of first through-holes 9 be small from this point of view as well. Preferably, only one first through-hole 9 is formed. At this time, the first through-hole 9 preferably has a size enough to supply a sufficient amount of culture solution to each channel.

Figure 3:
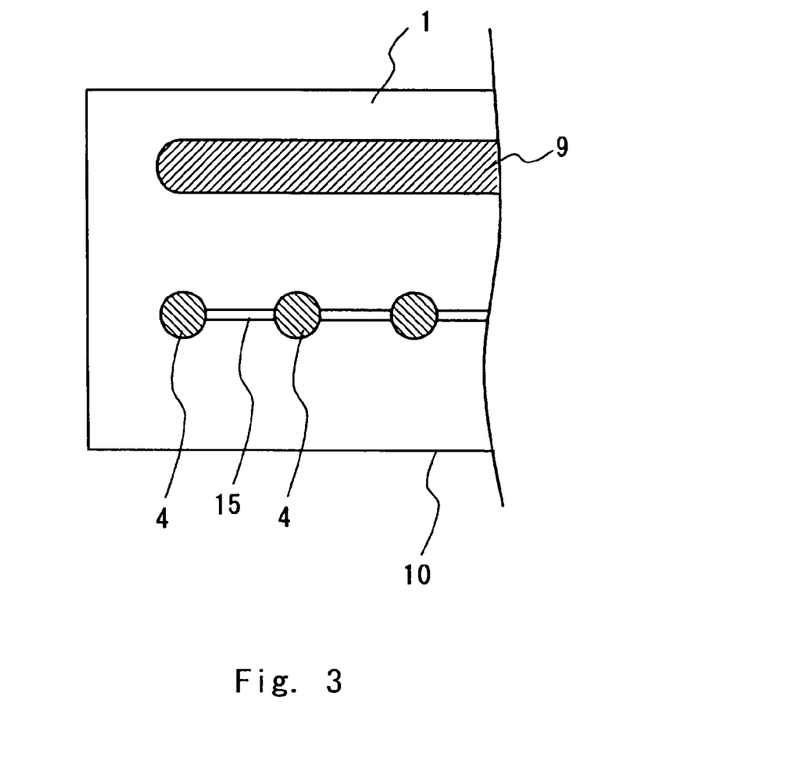
FIG. 3 shows the structure of a rear side of the microchannel array A of the present invention.

On the other hand, the second through-hole 4 is generally formed in every second recess 2 surrounded by the partition 5. In this case, plural second through-holes 4 are formed. FIG. 3 is a plan view showing the structure of the rear side of the first substrate 1 (the side opposite to the bond surface). As shown in FIG. 3, the first through-hole 9 and the second through-hole 4 are formed on the rear side of the first substrate 1. Plural second through-holes 4 as many as the second grooves 3 are formed. The adjacent second through-holes 4 communicate with each other through the third groove 15. Aside from this structure, for example, the second through-hole 4 may be formed in a third recess, and plural second through-holes 4 may be connected. As a result, the suction force is uniformly applied to the plural second through-holes 4, and a cell coat or the like can be prevented from being damaged due to excessive suction. Further, it is necessary to execute positional alignment between the suction port and the second through-holes 4 upon the suction. From this point of view as well, it is preferable that the second through-holes be connected together.

The diameter and width of the second through-hole 4 are preferably selected as appropriate within a range of 10 to 2,000 μm, more preferably, 20 to 1,000 μm in accordance with the number of microchannels and a requisite suction force level.

Examples of a method of manufacturing the microchannel array of the present invention include resin molding with a metal structure, precision machining, wet etching, dry etching, laser processing, and electric-discharge machining. An appropriate method is preferably selected from these manufacturing methods based on an application, requisite accuracy of finishing, and costs.

A method of manufacturing a resin mold through resin molding with the metal structure used as a mold enables copying the shape of the metal structure to the resin mold with high accuracy and excels in high dimensional accuracy. Further, a general-purposed resin material can be used to lower a material cost, so this method is appropriate for mass production. The above metal structure may be used as a metal mold as it is or may be set in a prepared metal mold when in use.

Examples of a manufacturing method of the metal structure include plating to a resist pattern formed through photolithography, precision machining, wet etching, dry etching, laser processing, and electric-discharge machining. Preferably, an appropriate method is selected based on an application, a requisite accuracy of finishing, a cost, or the like.

As a method of manufacturing a resin mold, for example, there are injection-molding, press-molding, monomer-cast molding, solvent-cast molding, hot emboss molding, and roll transfer based on extrusion molding. From the viewpoint of productivity and mold transferability, injection-molding is preferred. The injection-molding can produce 10000 to 50000 resin molds, 200000 resin molds under certain circumstances, from one metal structure, making it possible to considerably reduce a manufacturing cost of the metal structure. Further, a required period for 1 cycle of the injection-molding is as short as 5 to 30 seconds, so this method is very useful in terms of productivity. If multicavity-mold metal structure is used, the productivity can be more improved.

There is no particular limitation on a resin material. For example, an acrylic resin, a polylactic acid, polyglycolic acid, or styrene-based resin, a methacrylate/styrene copolymer resin (MS resin), a polycarbonate resin, a polyester resin such as polyethylene terephthalate, a polyvinyl alcohol resin, ethylene/vinyl alcohol copolymer resin, a thermoplastic elastomer such as styrene-based elastomer, a vinyl chloride resin, a silicone resin such as polydimethyl siloxane, and a polyvinyl butyral resin. These resins may optionally contain one or two or more of a lubricant, a light stabilizer, a thermal stabilizer, an anti-fogging agent, a pigment, a flame retardant, an antistatic agent, a mold lubricant, an anti-blocking agent, a UV absorber, and an antioxidant.

In the case of suction-trapping cells or other such particles, if the end surface of the first substrate and the second substrate is rough, there is a possibility that the cell coat is damaged when in contact with the surface. Thus, it is desirable to form the end surfaces as smoothly as possible. The method of smoothing the surface is appropriately selected based on a substrate material. If the substrate material is silicone, laser cutting and polishing in two steps with a not-fine dicing cutter and a fine dicing cutter are executed, for example. If the substrate material is a resin, fusing with thermal cutter, laser cutting, dicing, chamfering through machining, polishing, and the like are carried out.

A method of forming the first through-hole 9 and the second through-hole 4 is also selected as appropriate based on a substrate material. If the substrate material is silicone, laser cutting, wet etching, dry etching, sand blasting, and the like are carried out. If the substrate material is a resin, laser cutting, laser ablation, machining, and the like are carried out. A contact angle of the surface of the microchannel array of the present invention to water is preferably 0.5° or more and 70° or less, more preferably, 1° or more and 50° or less.

A space defined by the recesses and grooves of the microchannel array of the present invention can function as a flow path if having an affinity with an aqueous liquid such as a cell culture solution, a saline, a blood sample, and a reagent, that is, hydrophilic nature. If not hydrophilic, the aqueous liquid cannot flow through a flow path or hardly flows. Further, there is a fear that bubbles are mixed to hinder the flow of the aqueous liquid.

In particular, in the case of using a blood sample, the space should be hydrophilic. Blood cells in a blood component (erythrocyte, leucocyte, and blood platelet) tend to adhere to a hydrophobic surface. Thus, if the flow path surface is hydrophobic, the cells adhere to the flow path and clog the flow path in some cases.

For example, the contact angle of polymethylmethacrylate generally used as a substrate material to water is about 68°, the contact angle of a polycarbonate resin is about 70°, and the contact angle of a polystyrene resin is 84°. Under certain circumstances, an affinity imparting process should be executed to reduce the contact angle.

As a method of making a material surface hydrophilic, there are two broad categories: chemical treatment and physical treatment. Examples of the chemical treatment include chemical treatment, solvent treatment, coupling agent treatment, monomer coating, polymer coating, inorganic material coating, steam treatment, surface grafting, electrochemical treatment, and anodic oxidation. Examples of the physical treatment include UV application, plasma contact treatment, plasma jet treatment, plasma polymerization, vapor deposition polymerization, thermal oxidation, ion beam application, and mechanical treatment. Applicable treatment methods are described below.

Coating is a method of coating a material surface with a hydrophilic polymer (polyvinyl alcohol or the like) in an aqueous solution through, for example, dipping, spin-coating, or the like, and then drying the surface. If the microchannel array is too hydrophobic, there is a fear that a coating material is repelled by the surface, a uniform coating film thickness cannot be attained, and a reforming effect fluctuates. In some cases, a coating material needs to be selected. A material applicable to a hydrophobic surface is, for example, "Lipidure-PMB" (Lipidure-PMB) (copolymer of MPC polymer having a phospholipid polar group and butylacrylate) available from NOF Corporation. This method requires no large device and attains a beneficial effect through simpler steps, but has a possibility that coating is peeled off during ultrasonic washing or the like. In this case, it is preferred to coat the surface again or dispose of the cell before reuse.

Vacuum evaporation is a kind of steaming. This method heats a substance in a vacuum (at a pressure of $10^{-2}$ Pa or less) and vaporizes the substance to apply the steam to a desired material surface. This method does not require a large device and can process the target with the lower degree of vacuum. Thus, this method is advantageous in terms of costs.

Sputtering is a kind of plasma treatment. This method accelerates cations resulting from low-pressure glow discharge in an electric field to cause the cations to collide against a cathode to thereby spatter substances on the cathode side to cause the substances to deposit on the anode. This method can adopt a variety of materials. For example, an inorganic material such as $SiO_2$ or $Si_3N_4$ can be used. Further, the thus-completed product withstands ultrasonic washing and thus can be repeatedly used. Further, it excels in antisolvent property, so an elute does not damage the cells or the like. This method is thus applicable to the bioengineering field.

Further, sputtering enables uniform deposit film thickness. For example, if an inorganic material such as $SiO_2$ or $Si_3N_4$ is deposited to 10 nm to 300 nm to thereby attain a hydrophilic material surface. Further, if $SiO_2$ is deposited to 10 nm to 50 nm, a transparent and hydrophilic surface can be obtained.

To bring the material surface and the deposit film into close contact through sputtering, it is necessary to remove water from the material beforehand. In addition, it is effective to etch the material surface with argon gas or the like or predeposit an inorganic material such as chromium having high adherence.

In the case of executing sputtering, requisite heat-resistance temperature is about 50° C. to 110° C. Thus, if a thermoplastic resin is used as a material, it is necessary to meet conditions of (1) a thermoplastic resin having a glass transition temperature not less than the above temperature, for example, polycarbonate is selected, and (2) a sputtering period is shortened (film thickness is reduced).

Implantation is a kind of plasma treatment. This method activates, if a thermoplastic resin is used as a material, molecules of the material surface with plasma to recombine generated radicals to implant new functional groups into the material surface. According to this method, the material surface can be imparted with hydrophilic property and other properties.

Plasma polymerization is a kind of plasma treatment. This method vaporizes a monomer as a material of a polymer to vapor-phase transfer the vaporized one and activates the monomer through electron collision excitation in plasma to cause polymerization to form a polymer film on the material surface. This method is advantageous in that a film thickness can be easily controlled and unreacted monomer or solvent does not remain. Thus, the cell is not damaged with the unreacted monomer or solvent, and this method is applicable to the bioengineering field.

Vapor deposition polymerization is substantially the same as the above plasma polymerization except that a monomer is activated with heating to cause polymerization.

Thermal oxidation is a method of exposing, in the case of using silicone or other such inorganic materials, the material to the atmosphere under the high-temperature condition to thereby oxidize the material surface. In general, the material is exposed to an oxygen plasma atmosphere in a vacuum device to accelerate thermal oxidation.

Excimer UV treatment is a kind of UV irradiation treatment. The method applies, in the case of using a thermoplastic resin as a material, UV with a light emission center wavelength of 120 nm to 310 nm by use of an excimer lamp using a discharge gas such as argon, krypton, and xenon to dissociate molecules on the material surface to extract light hydrogen atoms to form highly hydrophilic functional groups such as a hydroxyl group. According to this method, a requisite heat resistance temperature for making the thermoplastic resin hydrophilic is low. Thus, this method is applicable to polymethylmethacrylate having a glass transition temperature of 100° C.

According to the excimer UV treatment, although a hydrophilic property is enhanced as an UV exposure amount increases, adhesion is imparted to the surface in some cases, resulting in another problem. Thus, an exposure amount should be adjusted in accordance with a requisite hydrophilic level.

As another method of forming a hydrophilic surface, there is a method of selecting an appropriate material. For example, if a blood cell is treated, it is necessary to not only immobilize the blood cell to the hydrophobic surface but also to suppress deposition of blood platelets to the surface due to blood coagulation. Examples of preferred materials include a material containing heparin preventing coagulation of blood platelets, a material where an enzyme urokinase that dissolves a blood platelet-derived thrombus is immobilized, a material covered with a polymer material having high water content such as polyvinyl alcohol, acrylamide, or polyethylene glycol, which can prevent deposition of blood platelets or protein to the surface, and a material covered with a micro phase separation structure that prevents activation of blood platelet. A final separation size of the micro phase separation structure is generally 20 nm to 20 μm, and a material of uniform microdomain structure is preferred. Such structure is realized by, for example, a combination of amorphous/amorphous, hydrophilic/hydrophobic, or crystalline/non-crystalline, glass/liquid materials. Specific examples thereof include a hydroxyethyl methacrylate (HEMA)-styrene copolymer, a HEMA-butadiene copolymer, a HEMA-styrene block copolymer, and a blend of crystalline nylon 610 and amorphous polypropylene oxide.

In addition, "EXCEVAL" available from Kuraray or polyvinyl butyral resin is preferred in some cases. In this case, to keep a fine groove shape, the temperature of the used aqueous solution is set to 70° C. or less, and an observation target should not be immersed in the water for long time.

One or both of the first substrate 1 and the second substrate 11 of the microchannel array of the present invention are preferably transparent. As a result, cells or other such particles and grooves or recesses of the microchannel array can be observed with a microscope with transmitted illumination or reflected epi-illumination, and micro-injection efficiency can be enhanced. An optical property that defines substrate transparency is a total transmittance of 80% or more and a haze value of 10% or less in the case of using a 1 mm-thick plate.

Further, if a high UV transmittance is required upon observation with a microscope, glass, especially, quartz glass is preferred as a material. If a thermoplastic resin is used, a material added no UV absorber or a material the molecular structure of which does not have an ability to absorb UV such as a ring system is preferred.

Regarding an outer size of the microchannel array of the present invention, the length and with are set to 100 mm or less in view of manufacturing costs, and an appropriate size is desirably selected in accordance with applications. The flatness of the microchannel array is preferably 1 μm or more from the viewpoint of industrial reproducibility, more preferably 200 μm or less in view of the microchannel array laminate as described below. Although not particularly limited, the microchannel array thickness is preferably 0.2 to 10 mm in view of damage, deformation, and distortion when in use. A dimensional accuracy of a shaping portion is within a range of ±0.5 to 10% of the thickness from the viewpoint of industrial reproducibility.

In the microchannel array of the present invention, plural first substrates are piled up in close contact while being aligned, and thus plural trap opening edges are formed in the length direction. That is, on the rear side of the first substrate 1, which is the side opposite to the bond surface of the second substrate 11, another first substrate 1 can be laminated. At this time, the substrates are laminated such that a surface having a groove of the additional first substrate 1 faces the second substrate. Thus, the first grooves 8 are arranged in the length direction of the first substrate 1, and the trap opening edges extend in the direction vertical to the bond surface. In this way, the micro-injection efficiency can be further enhanced by forming plural end surface 10 structures. The first substrate 1 is not limited to a two-layer structure, and three or more layers may be laminated.

As a positional alignment method of each substrate, there is a method of forming convex and concave patterns on the front and rear sides of the substrate and bringing the substrates into close contact with high positional accuracy, a method of fixing an outer edge of the substrate with a jig, a method of fixing the substrate by inserting a positioning pin to a through-hole, or a method of observing and positioning the substrate with an optical device such as a CCD camera or laser.

It is preferred that the additional first substrate 1 have the second through-hole 4 larger than the second through-hole 4 of the first substrate 1.

Along with the development of a high-density microchannel array, the second through-hole 4 of a smaller diameter is required. In this case, there is a possibility that upon micro-injection, a suction force enough to suck cells or other such particles cannot be obtained. On the first substrate 1; another first substrate having a second through-hole 4 the diameter of which is larger than that of the first substrate 1 is layered such that positions of the through-holes are aligned. Hence, even in the high-density microchannel array, a suction force necessary to suction-trap cells or other such particles can be obtained.

The microchannel array of the present invention uses a thermoplastic resin as a material and thus can be incinerated as infectious wastes similar to a thermoplastic resin of a blood circuit used in blood purification treatment such as artificial dialysis or plasma exchange. Such microchannel arrays can be burned up and overcome a problem of increasing an amount of wastes resulting from a single-use system. In addition, a resin substrate is laminated, so it is unnecessary to separate garbage according to type and to collectively burn the substrates. Further, a thermoplastic resin containing no halogen such as polymethylmethacrylate is used to prevent generation of dioxin as hazardous substance. The resin can be readily burned in an incinerator at ordinary temperature used in general waste incinerator and recycles as heat resources.

The microchannel array of the present invention supplies or extracts fluids such as a cell culture solution, a saline, a blood sample, or a reagent from an opening edge and thus is promising in the biotechnology field, the medical field, the agricultural field, and the industrial field.

If the microchannel array of the present invention is used to supply and extract cells or particles, the microchannel array can be expected to find its application to classification of cell and blood components, and to reaction and synthesis in the industrial field.

In the case where the microchannel array of the present invention is used to trap cells or particles, the microchannel array is expected to exert beneficial effects in the biotechnology field, especially, upon micro-injection.

The microchannel array of the present invention enables formation of oil-in-water type monodispersed fine particles or water-in-oil type monodispersed fine particles of uniform particle size and is expected to find application in the agricultural field, the medical field, the foods field, and the industrial field.

A dispersion phase as a particle is introduced to the end surface 10 from the second through-hole 4 through the second groove 3. Owing to a difference in wettability between the substrate surface and the dispersion phase, fine particles of uniform particular diameter can be formed. In the case of forming the oil-in-water type monodispersed fine particle, the substrate surface should be made hydrophilic. On the other hand, in the case of forming the water-in-oil type monodispersed fine particle, the surface should be made hydrophobic. Based on the method of controlling a control angle to the water, an appropriate one is selected.

It is possible to manufacture core shell type multilayer fine particles with the microchannel array of the present invention. A dispersion phase as an inner particle is introduced to the end surface 10 from the second through-hole 4 through the second groove 3. At the same time, a dispersion phase as an external particle is introduced to the end surface 10 from the first through-hole 9 through the first groove 8. As a result, core shell type multilayer fine particles of uniform particle size can be efficiently manufactured.

EXAMPLE

Next, the conventional micro chamber array and microchannel array and the coaxial microchannel array of the present invention are compared.

Production Example 1

Figure 9:
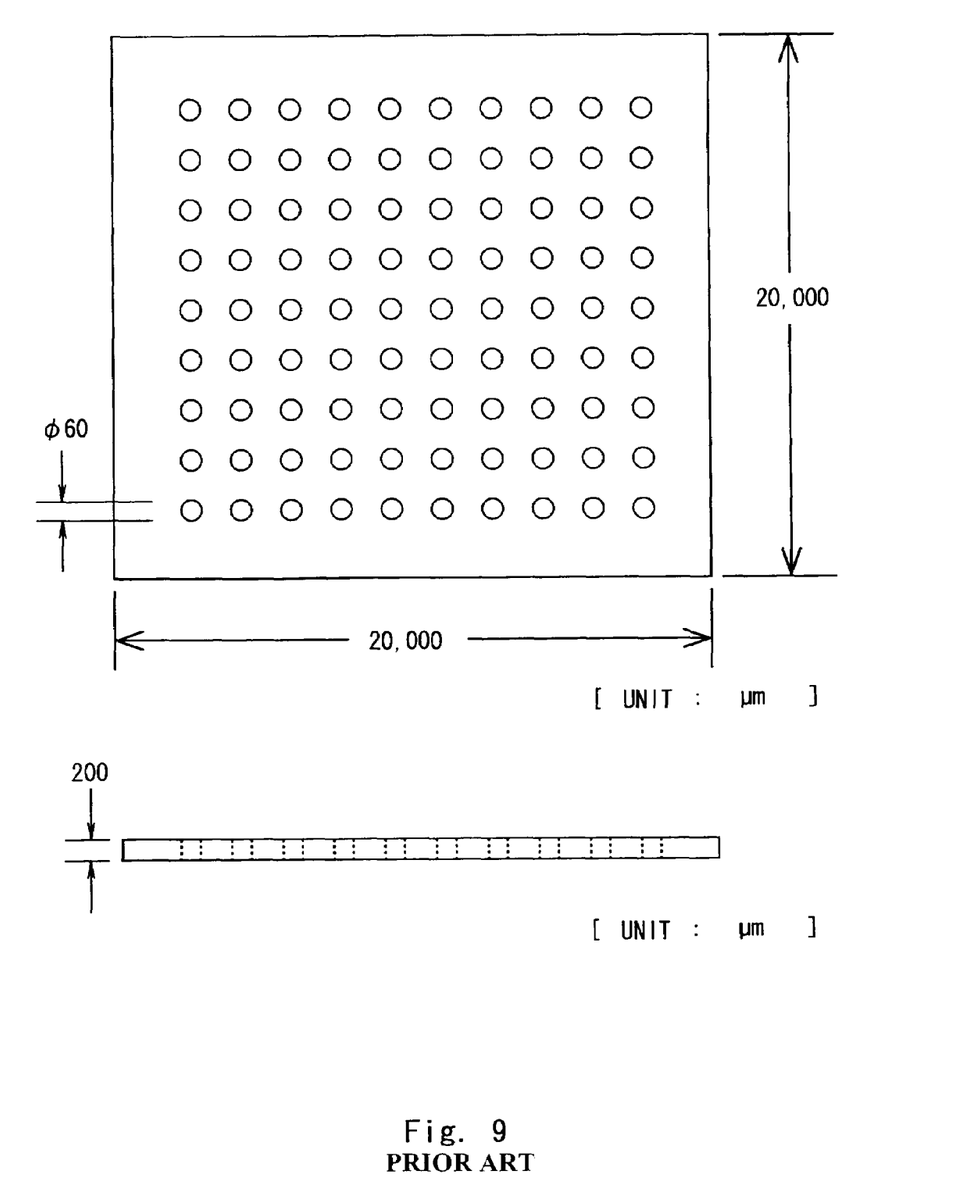
FIG. 9 shows a structure of a conventional micro chamber array.

Fabrication of Micro Chamber Array 100 through-holes having the diameter of 60 µm were formed in a 0.2-mm thick silicon substrate with the length of 20 mm and the width of 20 mm by use of a dry etching device available from Alcatel. The micro chamber array is used as Comparative Example. FIG. 9 shows the outer appearance of the micro chamber array.

Production Example 2

Figure 10:
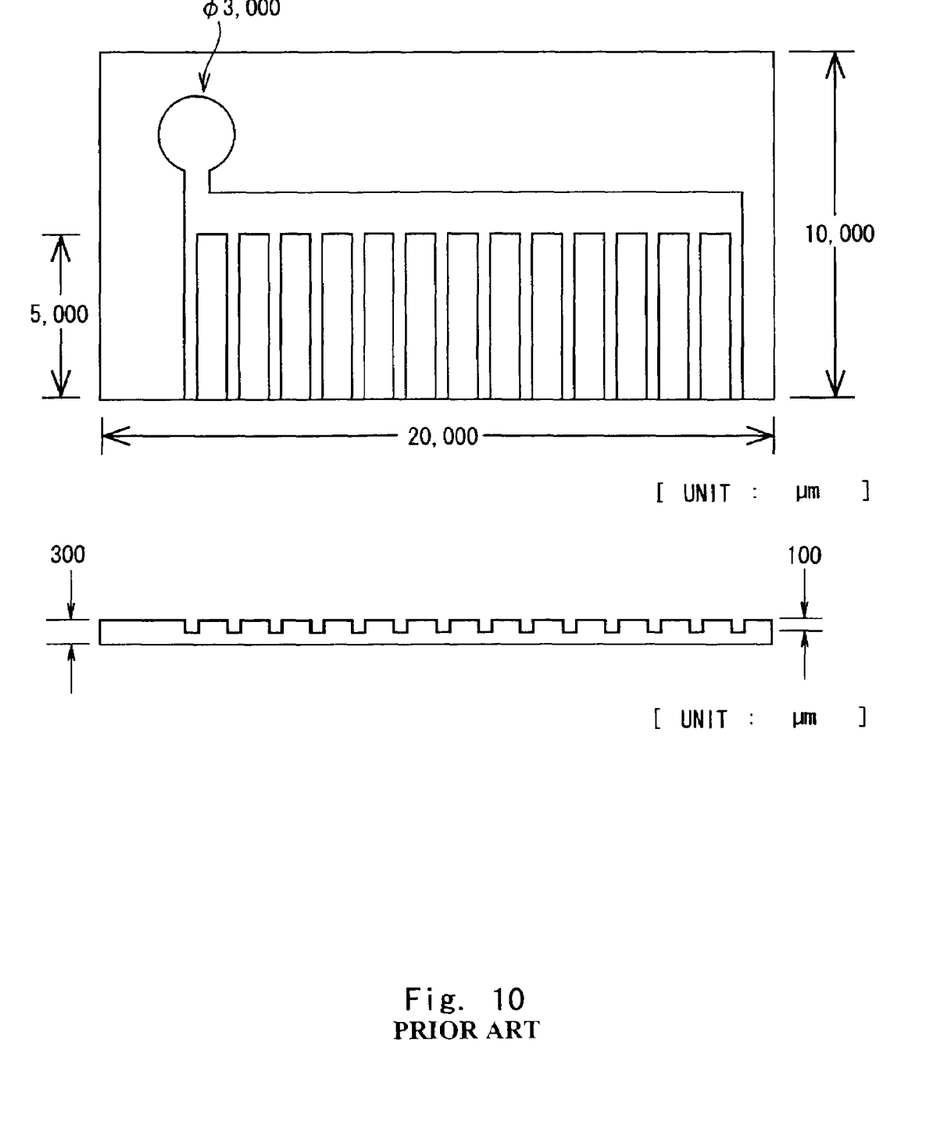
FIG. 10 shows a structure of a conventional micro chamber array.

Fabrication of Microchannel Array 14 channels having the width of 80 µm, the depth of 100 µm, and the length of 5000 µm were formed in a 0.3-mm thick silicon substrate with the length of 10 mm and the width of 20 mm by use of a dry etching device available from Alcatel. The channels communicated with each other through the grooves, and then a through-hole having the diameter of 3 mm was formed in the groove through sand blasting. Then, an acrylic substrate having the same size as that of the silicon substrate was brought into contact with the silicon substrate to complete a microchannel array. FIG. 10 is an outer appearance of the microchannel array.

Production Example 3

Coaxial Microchannel Array A

First, a resist pattern was formed on a glass plate through photolithography, and the resist pattern was subjected to plating to manufacture the metal structure. Next, the metal structure was used as a mould, and an acrylic resin (PARAPET G-HS) available from Kuraray was used as a material. A first substrate of a coaxial microchannel array A was manufactured through the injection-molding. Further, the through-hole (second through-hole 4) having the diameter of 0.3 mm was formed for sucking a cell on the substrate with a machining center. Finally, an acrylic substrate (second substrate) having substantially the same as that of the acrylic substrate was brought into close contact with the substrate to complete a coaxial microchannel array A of FIG. 1.

A shape of the coaxial microchannel array A has 20 microchannel pairs on a substrate having the width of 16 mm, the length of 8 mm, and the thickness of 1.0 mm. Each microchannel includes a first groove and a second groove through which a first through-hole, a second through-hole, a first recess, a second recess, a first recess, and a substrate end surface communicate with each other. The second groove 3 for sucking cells or the like has the width of 80 µm and the depth of 150 µm. The first grooves 8 for supplying a culture solution on both sides of the second groove 3 separated by the partition has the width of 100 µm and the depth of 150 µm. A positional relation between the boundary block 6 between the coaxial microchannels and the edge of the partition 5 at the edge of the end surface 10 is that the end surface 10 is at the same position as the edge of the boundary block 6, and the edge of the partition 5 is positioned 50 µm behind the edge of the boundary block 6.

Figure 4:
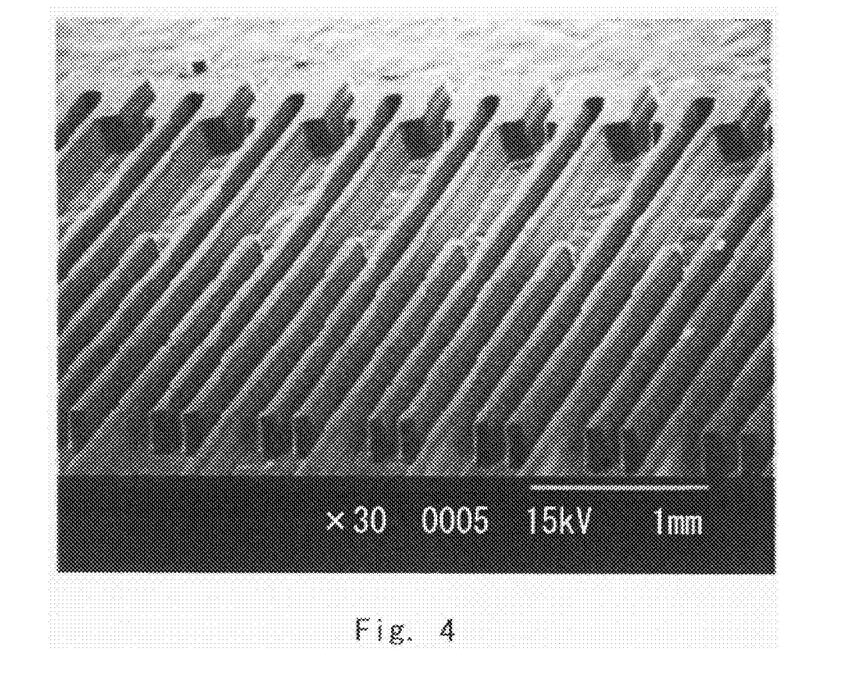
FIG. 4 is a scanning electron microscope (SEM) photograph of an outer appearance of the microchannel array A of the present invention.
Figure 5:
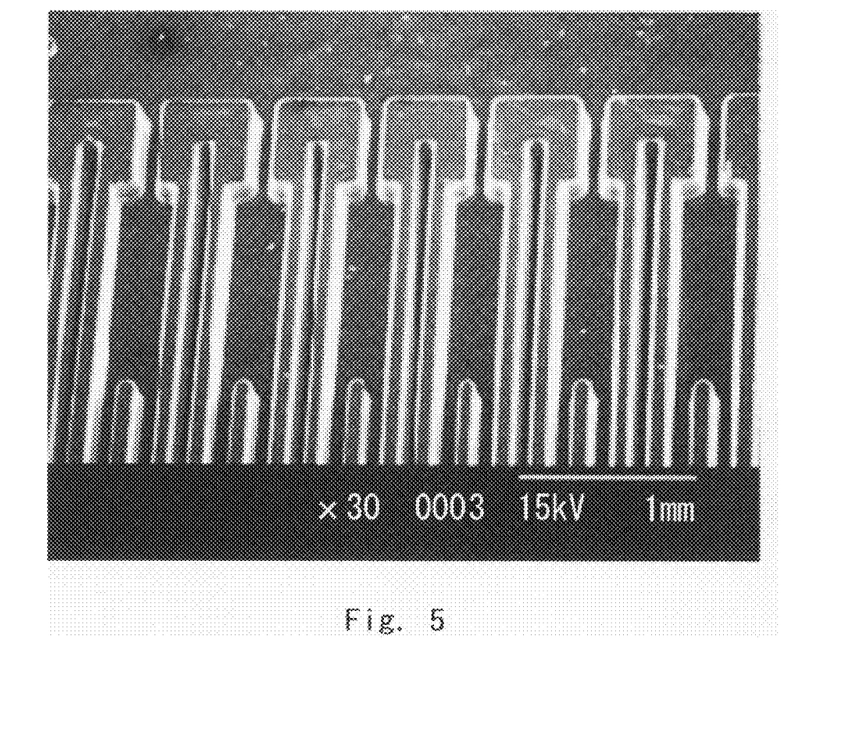
FIG. 5 is a SEM photograph of a microstructure of the center of the microchannel array A of the present invention.
Figure 6:
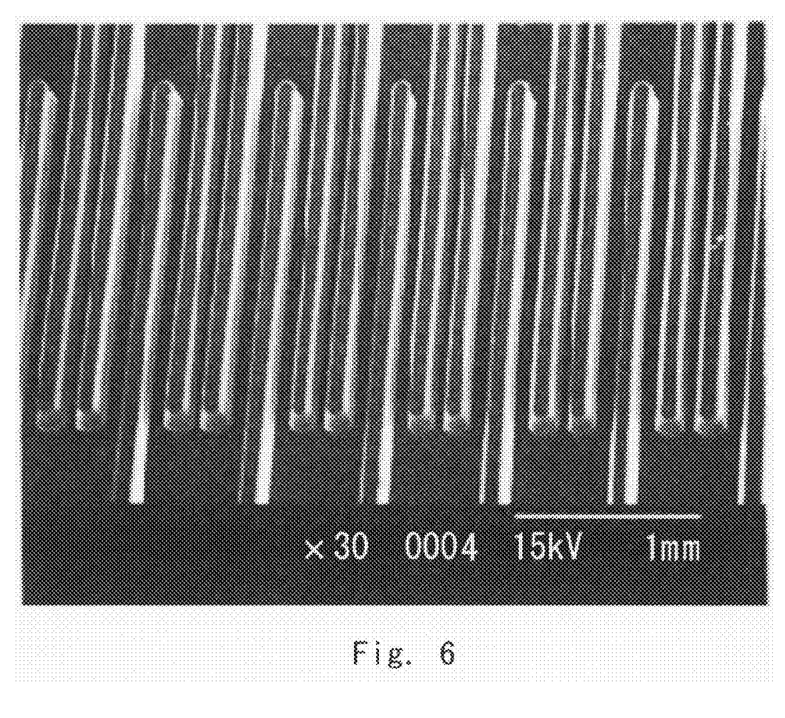
FIG. 6 is a SEM photograph of a microstructure of an end portion of the microchannel array A of the present invention.

A contact angle measuring apparatus (Kyowa Interface Science, CA-DT/A type) was used to measure a contact angle of the coaxial microchannel array A to the water in the air. The measurement result was 70°. Further, SEM observation of the coaxial microchannel array A was carried out. FIG. 4 shows the outer appearance, FIG. 5 shows the center of the fine structure, and FIG. 6 shows an end portion.

Production Example 4

Fabrication of Coaxial Microchannel Array B

The same process as that of Production Example 3 was carried out to fabricate a coaxial microchannel array B except that before the first substrate and the second substrate were brought into close contact, $SiO_2$ was deposited to 100 nm on both substrates to execute surface modification with a sputtering device (SV available from ULVAC). A result of measuring a contact angle of the coaxial microchannel array B to the water in the air was 11°.

Production Example 5

Fabrication of Coaxial Microchannel Array C

First, a glass substrate was subjected to precision machining with a micro cutting tool of the diameter of 100 μm to complete the metal structure. Next, the metal structure was used as a mould, and an acrylic resin (PARAPET G-HS) available from Kuraray was used as a material. A first substrate of a coaxial microchannel array C was manufactured through injection-molding. Further, a through-hole for sucking cells or the like, which has the diameter of 0.3 mm (second through-hole 4) was formed in the substrate through a machining center. Further, $SiO_2$ was deposited to 100 nm onto the first substrate and an acrylic substrate (second substrate) having substantially the same size as the first substrate for surface modification with a sputtering device (SV available from ULVAC). Finally, the two substrates were brought into close contact to complete a coaxial microchannel array C of FIG. 7.

Figure 7:
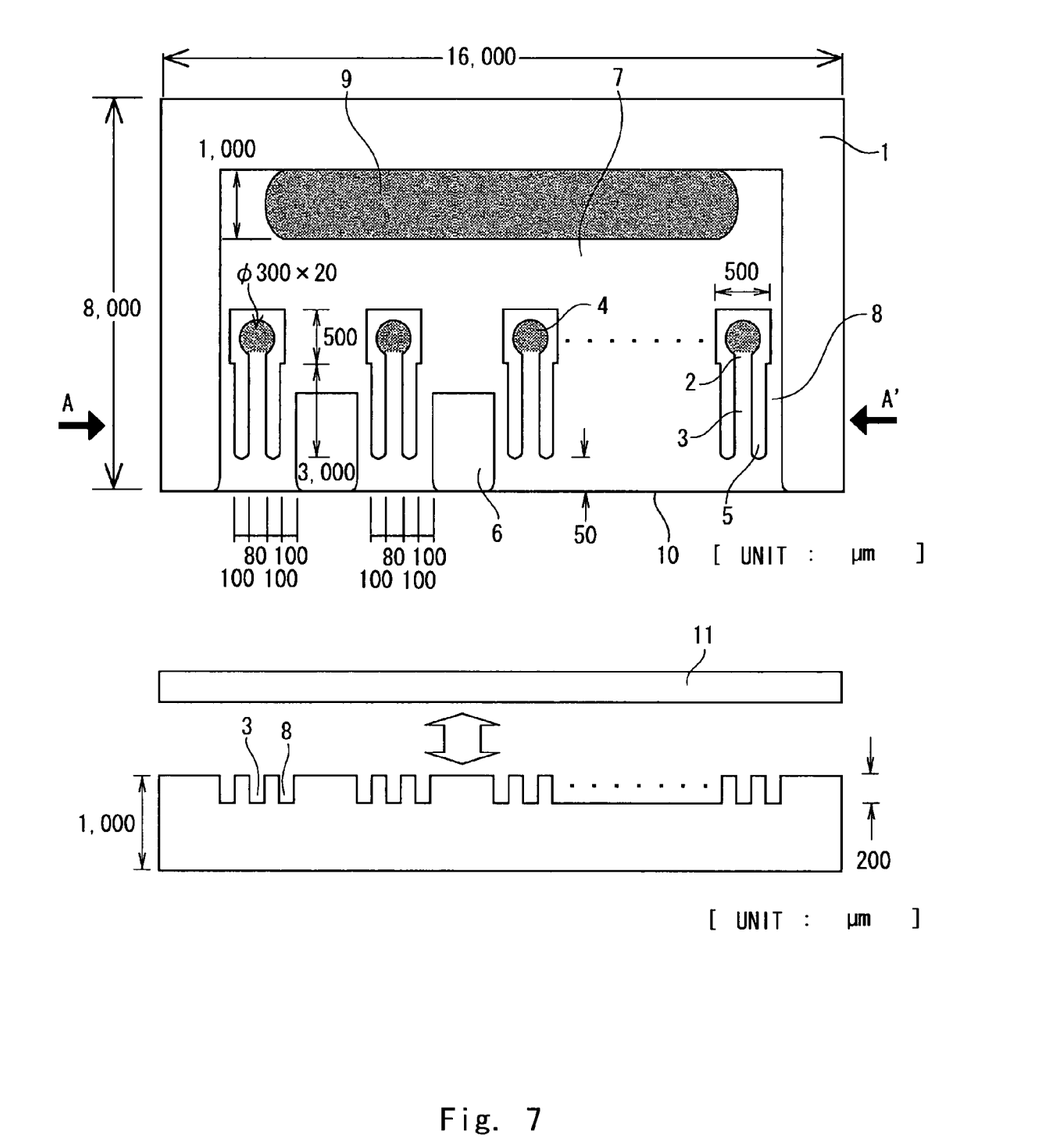
FIG. 7 shows a structure of array C of the present invention.

A shape of the coaxial microchannel array C is similar to a shape of the coaxial microchannel array A of Production Example 3 except that the depth of the second groove 3 for sucking cells or the like and the depth of the first grooves 8 for supplying a culture solution on both sides of the second groove 3 separated by the partition 5 were each 200 μm.

A result of measuring a contact angle of the coaxial microchannel array C to the water in the air was 15°.

Comparative Example 1

Micro-Injection with Micro Chamber Array

The micro chamber array manufactured in Production Example 1 was used to hold a bovine ova cell on the surface of the micro chamber array in a culture solution, followed by micro-injection. The micro chamber array made of silicone does not transmit visible light. Thus, the cell was observed with reflected epi-illumination, but the light was not reflected by a through-hole portion, and the cell could not be well observed.

Further, the probe movement direction and the observation direction of a microscope are substantially the same (vertical direction), and the probe is moved in the focal depth direction of the microscope. Thus, an image is blurred due to the movement and its positional control is difficult.

Comparative Example 2

Micro-Injection with Microchannel Array

The microchannel array manufactured in Production Example 2 was used to hold a bovine ova cell to the end surface of the microchannel array in a culture solution to carry out micro-injection. In a microchannel array that suction-traps cells or other such particles at an opening edge of the substrate end surface, the particle trap opening edge can be freely accessed from the outside to enable observation with a microscope with transmitted illumination and reflected epi-illumination. Further, a micropipette movement direction (substantially horizontal direction) and an observation direction of a microscope (vertical direction) are substantially orthogonal to each other. Thus, even when the micropipette was moved, the cell could be observed with high magnification.

However, the micro-injection is one of a series of processes such as suction-trap of cells in a culture solution, micro-injection, and cell incubation in a culture solution, and its efficiency is low. A cell differentation/proliferation speed in the culture solution was the same as that of the related art. An ova cell having a size of 100 μm was differentiated/proliferated up to about 200 μm after about 5 days. Further, the following problem remains to be solved. That is, if suction force necessary for trap is applied to a cell, the cell coat is damaged upon suction-trapping cells or other such particles to a particle opening edge.

Example 1

Micro-Injection with Coaxial Microchannel Array A

A bovine ova cell was immobilized in a culture solution containing the bovine ova cell with the coaxial microchannel array A manufactured in Production Example 3. As a result of observation with a microscope with transmitted illumination, it was observed that a bovine ova cell was trapped to an opening of the coaxial microchannel (second groove 3) of four coaxial microchannel pairs among 20 coaxial microchannel pairs. Bubbles were partially mixed in the second groove 3 and first groove 8 but did not influence the suction and culture solution supply. Since ova cells just after sampled were used, the cells were stabilized while supplied with fresh culture solution from the first groove 8 over 2 days.

Figure 8:
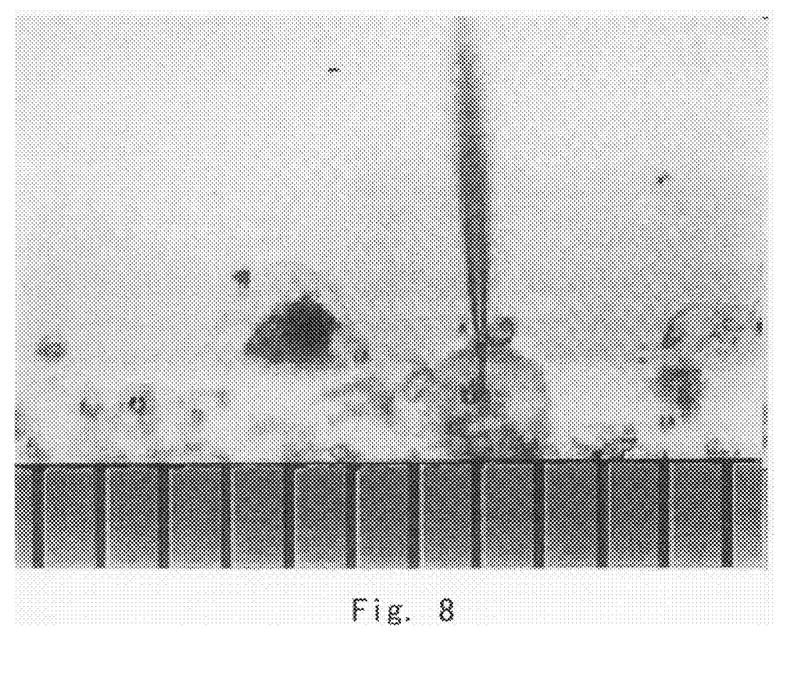
FIG. 8 is a microscope photograph of how a substance is injected through micro-injection using the microchannel array A of the present invention.

Next, micro-injection was carried out through observation with a microscope with transmitted illumination. The micropipette movement direction (substantially horizontal direction) and the observation direction of a microscope (vertical direction) are substantially orthogonal to each other. Thus, the cell could be observed with high magnification, and a probe could be injected to the depth optimum for the cell coat of one ova cell without damaging the ova cell. FIG. 8 is a microscope photograph of the cell and coaxial microchannel array A upon micro-injection. The cell could be sucked from the second groove 3 formed in the lower first substrate 1. Then, a culture solution could be supplied from the first grooves 8 on both sides thereof. A substance such as gene could be injected to the cell with a cell-insertion glass micropipette.

Next, as a result of carrying out differentiation/proliferation of a bovine ova cell in a coaxial microchannel, it was confirmed that 100-μm ova cell grew to about 200 μm in third day. Under such environment that a fresh culture solution is continuously supplied from the first groove 8, the cell was cultured in a narrow space having the height of 150 μm and the depth of 50 µm, with the result that the cell differentation/proliferation speed could increase.

A series of processes, stabilization, micro-injection, and cell differentation/proliferation in a culture solution can be carried out by using the coaxial microchannel array, and micro-injection efficiency can be drastically improved. Further, the reason the trapped ova cell could be held without damaging its cell coat over a few days is that the ova cell could be immobilized with the minimum suction force in a small.

Example 2

Micro-Injection with Coaxial Microchannel Array B

Similar to Example 1, a series of processes, stabilization, micro-injection, and cell differentation/proliferation in a culture solution were executed with the coaxial microchannel array B fabricated in Production Example 4. As a result, similar to the coaxial microchannel array A, the micro-injection efficiency could be drastically improved, and the mixture of bubbles observed in Example 1 did not occur in this Example, and bubbles could be completely eliminated through an affinity imparting process.

Example 3

Micro-Injection with Coaxial Microchannel Array C

The coaxial microchannel array C obtained in Production Example 5 was used to execute a series of processes, stabilization, micro-injection, and cell differentation/proliferation in culture solution, similar to Example 1. Similar to the coaxial microchannel array B, the micro-injection efficiency could be drastically enhanced, and bubbles could be completely removed in an affinity imparting process. On the other hand, 100 µm ova cell grew to about 200 µm through differentation/proliferation over 4 days that is 1 day longer than Examples 1 and 2. It is supposedly because the space height is as large as 200 µm, and an appropriate space size needs to be selected in accordance with a target cell size.

INDUSTRIAL APPLICABILITY

According to the present invention, a microchannel array capable of increasing a cell differentation/proliferation speed can be provided.

The invention claimed is:

1. A microchannel array containing a first substrate, and a second substrate bonded to the first substrate with a particle trap opening edge being formed in an front end surface of the first substrate by a groove formed in a bond surface of the first substrate, comprising:
   (a) a first through-hole passed through the first substrate, a first recess including the first through-hole, and a plurality of first grooves communicating with the first recess and the front end surface of the first substrate, wherein each of the first grooves are split by a boundary block partition stretching along the first groove;
   (b) a second through-hole passed through the first substrate, a second recess having the second through-hole, and a second groove communicating with the second recess and the front end surface of the first substrate, wherein the second groove comprises the second recess and the second through-hole at one end with the second end being in the vicinity of the front end surface of the first substrate; and
   (c) a second partition separating the first recess from the second recess, at the bond surface of the first substrate, wherein the second groove is formed between the plurality of adjacent first grooves with the second partition between the second groove and the first grooves, and wherein the first through-hole is spatially separated from the plurality of the first grooves and the second groove, and is located in the rear end surface of the first substrate and the second through-hole is located between the first through-hole and the front end surface of the first substrate.

2. The microchannel array according to claim 1, wherein a width and depth of the first groove is 0.1 to 300 µm, and a ratio between the width and depth of the first groove is 1:10 to 10:1.

3. The microchannel array according to claim 1, wherein a width and depth of the second groove is 0.1 to 300 µm, and a ratio between the width and depth of the second groove is 1:10 to 10:1.

4. The microchannel array according to claim 1, wherein the plurality of adjacent first grooves, the second groove formed between the first groups with the second partition between the first group and the second group, and the second recess corresponding to the second groove constitute a microchannel group, and a plurality of microchannel groups are arranged along the front end surface of the first substrate.

5. The microchannel array according to claim 4, wherein the second through-holes in the second recesses of the plurality of microchannel groups are connected on a rear side of the first substrate by a third groove.

6. The microchannel array according to claim 1, wherein a contact angle of the surface to water is 0.5° or more and 70° or less.

7. The microchannel array according to claim 1, wherein at least one of the first substrate and the second substrate is a transparent substrate.

8. The microchannel array according to claim 1, further comprising:
   at least one additional first substrate bonded to the first substrate, wherein a plurality of particle trap opening edges extend in a direction vertical to the bond surface, at the front end surfaces of the plurality of first substrates.

9. The microchannel array according to claim 8, the second through-hole in the additional first substrate is larger than the second through-hole in the first substrate.

10. The microchannel array according to claim 1, wherein a fluid is supplied/extracted to/from the front end surface of the first substrate through at least one of the first groove and the second groove of the microchannel array.

11. The microchannel array according to claim 1, comprising a plurality of the second through-holes and a plurality of the second grooves communicating with the second recess and the front end surface of the first substrate.

* * * * *